United States Patent
Lin et al.

(10) Patent No.: US 11,209,425 B2
(45) Date of Patent: Dec. 28, 2021

(54) QUANTITATION OF FUNCTIONAL GROUPS ON SOLID SUPPORTS

(71) Applicant: Siemens Healthcare Diagnostics Inc., Tarrytown, NY (US)

(72) Inventors: Spencer Lin, San Diego, CA (US); Christopher Reamer, Brewster, NY (US); Ryan Spears, Stamford, CT (US)

(73) Assignee: Siemens Healthcare Diagnostic Inc., Tarrytown, NY (US)

( * ) Notice: Subject to any disclaimer, the term of this patent is extended or adjusted under 35 U.S.C. 154(b) by 346 days.

(21) Appl. No.: 15/557,078

(22) PCT Filed: Mar. 10, 2016

(86) PCT No.: PCT/US2016/021741
§ 371 (c)(1),
(2) Date: Sep. 8, 2017

(87) PCT Pub. No.: WO2016/145174
PCT Pub. Date: Sep. 15, 2016

(65) Prior Publication Data
US 2018/0045716 A1    Feb. 15, 2018

Related U.S. Application Data

(60) Provisional application No. 62/130,863, filed on Mar. 10, 2015.

(51) Int. Cl.
| | | |
|---|---|---|
| *G01N 33/531* | (2006.01) | |
| *G01N 33/536* | (2006.01) | |
| *G01N 33/543* | (2006.01) | |
| *G01N 33/52* | (2006.01) | |

(52) U.S. Cl.
CPC ........... *G01N 33/531* (2013.01); *G01N 33/52* (2013.01); *G01N 33/536* (2013.01); *G01N 33/54306* (2013.01); *G01N 33/54353* (2013.01)

(58) Field of Classification Search
CPC .... G01N 33/52; G01N 33/531; G01N 33/536; G01N 33/54306; G01N 33/54353
See application file for complete search history.

(56) References Cited

U.S. PATENT DOCUMENTS

| | | | |
|---|---|---|---|
| 4,661,408 A | 4/1987 | Lau et al. | |
| 5,898,005 A | 4/1999 | Singh et al. | |
| 6,231,982 B1 | 5/2001 | Wang | |
| 7,842,475 B2 | 11/2010 | Zheng et al. | |
| 2003/0194799 A1* | 10/2003 | Achter | B03C 1/288 435/287.2 |
| 2007/0141714 A1 | 6/2007 | Sung et al. | |
| 2007/0248990 A1 | 10/2007 | Remacle et al. | |
| 2009/0170070 A1 | 7/2009 | Neerken et al. | |
| 2012/0315621 A1 | 12/2012 | Lu et al. | |
| 2013/0029428 A1 | 1/2013 | Kim et al. | |

FOREIGN PATENT DOCUMENTS

| | | |
|---|---|---|
| CN | 101467045 A | 6/2009 |
| CN | 102859359 A | 1/2013 |

OTHER PUBLICATIONS

Hennig et al., "Simple Colorimetric Method for Quantification of Surface Carboxy Groups on Polymer Particles," Anal. Chem., 2011, vol. 83, No. 12, pp. 4970-4974.*
Ghasemi et al., "Determination of Amine and Aldehyde Surface Densities: Application to the Study of Aged Plasma Treated Polyethylene Films," Langmuir, 2007, vol. 23, No. 23, pp. 11554-11561.*
Rozkiewicz et al., "Reversible Covalent Patterning of Self-Assembled Monolayers on Gold and Silicon Oxide Surfaces," Langmuir, 2005, vol. 21, No. 14, pp. 6337-6343.*
Moon et al., "Absolute Surface Density of the Amine Group of the Aminosilylated Thin Layers: Ultraviolet-Visible Spectroscopy, Second Harmonic Generation, and Synchrotron-Radiation Photoelectron Spectroscopy Study," Langmuir, 1997, vol. 13, No. 16, pp. 4305-4310.*
Andreas Henning et al: "Quantification of surface functional groups on polymer microspheres bysupramolecular host-guest interactions", Chem Comm, vol. 47, pp. 7842-7844; www.rsc.org/chemcomm; Dynamic Article Links / Jan. 1, 2011.
Jason J. Cournoyer et al: "Color Test for the Detection of Resin-Bound Aldehyde in Solid-Phase Combinatorial Synthesis", Journal of Combinatorial Chemistry., vol. 4, No. 2, Mar. 1, 2002 (Mar. 1, 2002), pp. 120-124, XP055461112, US ISSN: 1520-4766, DOI: 10.1021/cc010060g.
Anonymous: "Instructions TNBSA (2,4,6-Trinitrobenzene Sulfonic Acid) from Thermo scientific", Jan. 1, 2008 (Jan. 1, 2008), pp. 1-2, XP055461167, Retrieved from the Internet: URL:https://assets.thermofisher.com/TFS-Assets/BID/manuals/000386-.pdf.
PCT Search Report and Written Opinion for International Application No. PCT/US2016/021741, dated Jul. 21, 2016.
Qiu Shenghui et al.: "Quantification of the Content of the Primary Amino Groups on Superparamagnetic Nanoparticles with Iminothiolane"; Journal of Engineering Technology and Education, ISSN 1813-3851, p. 253-261 (2013) (See English Abstract).
Qu Zhengyuan et al.:"A facile, one-step method for the determination of accessible surface primary amino groups on solid carriers"; Surf. Interface Anal., vol. 44, pp. 1309-1313; (2012).

* cited by examiner

*Primary Examiner* — Galina M. Yakovleva

(57) ABSTRACT

Processes for quantifying an amount of functional groups immobilized on a solid support are described herein. The processes allow for determining whether sufficient functional groups are provided on a solid support for the attachment of a first binding pair member for the detection of a target analyte.

8 Claims, 8 Drawing Sheets

QUANTITATION OF FUNCTIONAL GROUPS ON SOLID SUPPORTS

FIELD OF THE INVENTION

The present invention relates to the field of diagnostic testing, and more particularly to methods for quantifying functional groups immobilized on a solid support.

BACKGROUND OF THE INVENTION

In the fields of medicine and clinical chemistry, many studies and determinations of physiologically reactive species or analytes are carried out by taking advantage of the interaction between specific binding pair members. For example, the target analyte in a patient sample may itself be one member of a specific binding pair, which may be detected by employing a corresponding member of the specific binding pair immobilized on a solid support. In this case, the immobilized binding pair member may be an antigen for the detection of a target antibody in a sample, for example. Various solid support materials have been developed for these applications and require various bonding techniques to immobilize the specific binding pair member on the solid support.

For example, paramagnetic particles (PMP) are known solid support materials which may be functionalized with functional groups such as amine functional groups. In some instances, these functional groups may be selected so as to bond with a linking group (e.g., glutaraldehyde), which bonds to a binding pair member. The binding pair member may be selective for a target analyte in a sample, which is typically a second member of the binding pair as mentioned above. In immobilizing the binding pair member on the solid support, it may be necessary to ensure a proper amount of the functional groups are available for direct or indirect attachment of the binding pair member. Too few available functional groups, for example, may result in too few attachment sites when the binding pair member is added. This may result in a solid support incapable of accurately determining an amount of a target analyte at certain concentrations, particularly at higher concentrations in the detectable range of the target analyte. On the other hand, providing greater concentrations of the functional groups for the immobilization of the specific binding member may substantially increase production costs without any added benefit.

Accordingly, there is a need to determine and/or confirm the number of functional groups, directly or indirectly, present on a solid support to in order to optimally immobilize the specific binding pair members to the solid support. While there are known methods for quantitatively determine an amount of functional groups in solution, such methods are typically unsuitable for solid supports since colored or fluorescent reaction products formed in such quantification methods typically bind to the solid support, thereby rendering detection and quantitation difficult and/or impossible.

BRIEF DESCRIPTION OF THE DRAWINGS

Aspects of the invention are explained in the following description in view of the drawings that show.

DETAILED DESCRIPTION OF THE INVENTION

In accordance with an aspect of the present invention, there are provided processes for quantifying an amount of functional groups immobilized on a solid support. In certain aspects, the processes allow for the determination of an optimal number of functional groups to be disposed on a solid support during manufacture of a solid support product. In this way, waste may be eliminated and/or reduced, and performance of the solid support may be improved upon. For example, by quantifying the number of functional groups available on a solid support, it can be assured that adequate functional groups are available for direct or indirect attachment of a first member of a specific binding pair. Thereafter, like solid supports can be manufactured with an optimized loading of the specific binding pair member. In certain embodiments, the processes described herein thus allow for the quantitation of available functional groups prior to the direct or indirect attachment of one member of a specific binding pair provided on the solid support.

As used herein, the term "about" refers to a value that is ±10% of the stated value.

As used herein, the terms "attachment," "binding," "immobilized," "linking," or the like are understood not to be limited to covalent bonding, and may include any type of attraction, affinity, conformational selection, induced fit, or bonding between two or more molecules.

As used herein, by the phrase "effective amount," it is meant an amount of material suitable for bringing about an intended result.

As used herein, the term "sample" includes any sample having or suspected of having the target analyte, and may be a biological or non-biological sample.

As used herein, the term "subject" refers to any human or non-human mammal.

Figure 1:
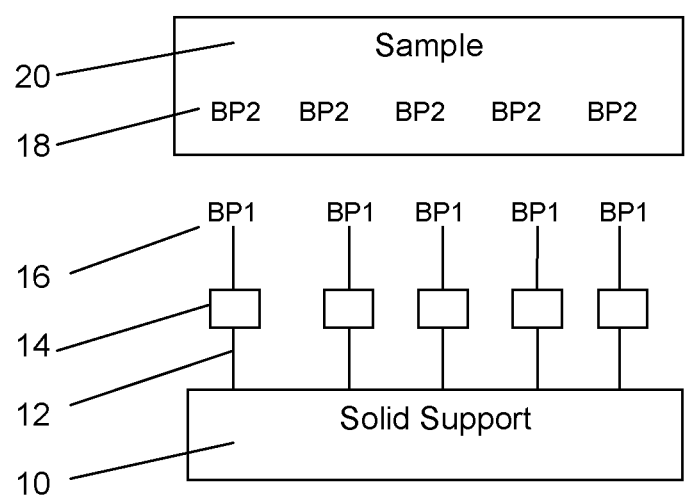
FIG. 1 illustrates a prior art solid support having a first binding pair member immobilized thereon for detection of a second complementary binding pair member in a sample in accordance with an aspect of the present invention.

Referring to FIG. 1, there is shown an exemplary solid support 10 having surface functional groups 12 on a surface thereof. In the embodiment shown, there is also provided a linking agent 14 for the immobilization of a first binding pair member 16 to the solid support 10. It is understood however that the present invention does not require such a linking agent 14, and that the first binding pair member 16 may instead be bonded directly to the surface functional groups 12. The first binding pair member 16 may be suitable for conjugation with a second binding pair member 18 in a sample 20 as shown. The sample 20 may be a standard sample, or a sample (e.g., biological sample) suspected of having the second binding pair member 18. As such, the second binding pair member 18 may be considered a target analyte for the solid support 10.

The solid support 10 may be comprised of an organic or inorganic water insoluble and impermeable material, which may also be transparent or partially transparent. In addition, the solid support 10 may be in the form of a bead, particle, fiber, film, membrane, tube, well, a strip, rod, a planar surface such as a plate, and the like. Depending on the type of assay for which the solid support 10 is intended to be used, the solid support 10 may or may not be suspendable in the medium in which it is employed. Examples of suspendable supports include but are not limited to polymeric materials such as latex, lipid bilayers or liposomes, oil droplets, cells and hydrogels, magnetic particles, and the like. Other solid support materials include polymers, such as nitrocellulose, cellulose acetate, poly (vinyl chloride), polyacrylamide, polyacrylate, polyethylene, polypropylene, poly (4-methylbutene), polystyrene, polymethacrylate, poly(ethylene terephthalate), nylon, poly(vinyl butyrate), etc.; either used alone or in conjunction with other materials.

In certain embodiments, the solid support 10 comprises one or more solid particles. When in the form of particles, the particles may have an average diameter of at least about 0.02 microns to about 100 microns, for example. In particular embodiments, solid particles may have an average diameter from about 0.05 microns to about 20 microns, or from about 0.3 microns to about 10 microns. In addition, the particles may have a surface area range of about 10 to about 100 m$^2$/g, and in some embodiments the particles may have a surface area in the range of about 10 to about 60 m$^2$/g. The particle may be organic or inorganic, swellable or non-swellable, porous or non-porous, and may have a density approximating water, generally from about 0.7 g/mL to about 1.5 g/mL, and composed of material that can be transparent, partially transparent, or opaque.

The particles may have a regular or irregular shape. They may be, for example, spheres, spheroids or spheres possessing cavities or pores. The particles may comprise several layers, such as what are termed core and shell particles, having a core and one or more enveloping layers. In certain embodiments, the particles may be formed from biological materials such as cells and microorganisms, e.g., erythrocytes, leukocytes, lymphocytes, hybridomas, streptococcus, *Staphylococcus aureus, E. coli,* viruses, and the like. The particles can also be particles comprised of organic and inorganic polymers, liposomes, latex particles, magnetic or non-magnetic particles, phospholipid vesicles, chylomicrons, lipoproteins, dye crystals, metal sols, silica particles, glass particles, magnetic particles, oil drops, lipid particles, dextran and protein aggregates and the like.

In certain embodiments, the particles comprise nanoparticles and/or microparticles. Such particles may have an approximate diameter of at least about 20 nm and not more than about 20 microns, or between 40 nm and 10 microns, or between 0.1 and 10 microns, or between 0.1 and 5 microns, or between 0.15 and 2 microns. In particular embodiments, the microparticles may be particles that are suspended in aqueous solutions.

The particles may comprise polymer particles that can be dispersed and/or suspended within an aqueous solution. In certain embodiments, the particles may be readily dispersible in an aqueous medium, and can be adsorptive or functionalizable as will be explained below so as to permit conjugation to a member of a specific binding pair, either directly or indirectly (through a linking agent). The particles may also be derived from naturally occurring materials, naturally occurring materials that are synthetically modified, and synthetic materials. Exemplary organic polymers include polysaccharides, particularly cross-linked polysaccharides, such as agarose, which is available as SEPHAROSE® (Cytiva, Marlborough, Mass.); dextran, available as SEPHADEX® and SEPHACRYL® (GE Healthcare, Chicago, Ill.); cellulose, starch, and the like; addition polymers, such as polystyrene, polyvinyl alcohol, homopolymers and copolymers of derivatives of acrylate and methacrylate, such as esters and amides having free hydroxyl functionalities, and the like.

In certain embodiments, the solid support 10 comprises one or more magnetic particles such as paramagnetic particles. When the particles are magnetic, the magnetic material contained in the particles may be any magnetic material susceptible to attraction by a permanent magnet or an electromagnet. Examples of such magnetic materials include magnetic iron oxides, magnetic chromium dioxides ($CrO_2$), $MnFeO_4$, $ZnFeO_4$, $CoFe_2O_4$, and similar magnetic materials.

Further exemplary magnetic particles for use with the solid support 10 include those that have a magnetic core surrounded by a polymeric material. The polymeric material may be any polymeric material suitable for use in assays such as polystyrene and polystyrene-divinyl benzene. In other embodiments, the magnetic particles may comprise chromium dioxide magnetic particles (chrome particles). As will be discussed further below, these particles may have pendent surface groups such as amine functional groups which are aldehyde-reactive, or which can be modified to include aldehyde-reactive groups.

Exemplary chromium oxide particles include those comprising a core of chromium oxide that has a reduced surface, which is then coated with silica and further coated with a silane as taught in U.S. Pat. No. 4,661,408, the relevant disclosure of which is incorporated herein by reference. Other particular embodiments of magnetic and non-magnetic particles that may be employed are set forth in U.S. Pat. No. 6,231,982, the relevant disclosure of which is also incorporated herein by reference.

The solid support 10 may comprise or otherwise be modified so as to include surface functional groups 12 which are bound (by covalent bonding or otherwise) to the solid support 10, and which may bind to a first binding pair member 16 directly or via a linking agent, e.g., linking agent 14. In the latter case, the solid support 10 includes surface functional groups 12, which bind to one or more linking agents 14. Each linking agent 14 may, in turn, bind to one or more first specific binding pair members 16. Exemplary suitable surface functional groups 12 include amine, hydrazine, hydrazide, aminooxy, cyanide, alcohol groups, and the like. In particular embodiments, the surface functional groups 12 comprise amine functional groups.

In certain embodiments, as shown in FIG. 1, one or more linking agents 14 may be utilized between the functional groups 12 on the solid support 10 to immobilize one or more first binding pair members 16 on the solid support 10. In certain embodiments, the linking agent 14 comprises one or more members from the group consisting of carbon, oxygen, sulfur, nitrogen, and phosphorous. In addition, the linking agent 14 may be aliphatic or aromatic. When heteroatoms are present, oxygen may be present as oxo or oxy, bonded to carbon, sulfur, nitrogen or phosphorous; nitrogen may be present as nitro, nitroso or amino, and bonded to carbon, oxygen, sulfur or phosphorous; sulfur may be analogous to oxygen; while phosphorous may be bonded to carbon, sulfur, oxygen or nitrogen, usually as phosphonate and phosphate mono- or diester. In certain embodiments, any compound useful in forming a bond between the first binding pair member 16 and functional groups 12 on the solid support 10 may be utilized as the linking agent 14.

Additional exemplary linking agents 14 include but are not limited to aldehydes, dicarboxylic acids and anhydrides, polyamines, polyaldehydes, and heterobifunctional agents such as 2-iminothiolane hydrochloride, sulfosuccinimidyl-4-(N-maleimidomethyl)cyclohexane-1-carboxylate, m-maleimidosuccin-imide ester, N-succinimidyl-(4-iodoacetyl) aminobenzoate, and similar species known to those skilled in the art.

Further linking agents 14 may include compounds comprising a nitrogen group, a phosphate group; an amino group; an alkylating agent such as halo or tosylalkyl, oxy (hydroxyl or the sulfur analog, mercapto); oxocarbonyl (e.g., aldehyde or ketone); or active olefin such as a vinyl sulfone or α-, β-unsaturated ester. In an embodiment, these linking agents 14 may immobilize the first binding pair member 16 on the solid support 10 by reaction with the surface functional groups 12 and the first binding pair member 16. Where an amine and a carboxylic acid or its nitrogen derivative or phosphoric acid are reacted, amides, amidines, and phosphoramides are formed. Where mercaptan and activated olefin are linked, thioethers are formed. Where a mercaptan and an alkylating agent are linked, thioethers are formed. Where an aldehyde and an amine are linked under reducing conditions, an alkylamine is formed. Where a ketone or aldehyde and a hydroxylamine (including derivatives thereof where a substituent is in place of the hydrogen of the hydroxyl group) are linked, an oxime functionality (=N—O—) is formed. Where a carboxylic acid or phosphate acid and an alcohol are linked, esters are formed. Various linking agents that may be utilized herein are known in the art; see, for example, Cautrecasas, J. Biol. Chem. (1970) 245:3059.

In a particular embodiment, the linking agent 14 is one that will react with amine groups on the solid support 10 on the one hand and react with amine groups of the first binding pair member 16 on the other hand. Thus, in certain embodiments, the linking agent 14 may comprise an aldehyde such as glutaraldehyde which includes at least two reactive carbonyl groups—one of which will react with the functional groups 12 on the solid support 10 and one which will react with the first binding pair member 16.

The first specific binding pair member 16 may include any compound which is selective for a target analyte in a sample, such as a corresponding second binding pair member 18. In an embodiment, the first binding pair member 16 may thus comprise any member of a pair of components, which may bond or otherwise bind via an attractive force, fit, or the like with at least a second member of the specific binding pair. In a certain embodiment, the first binding pair member 16 may bind to more than one second binding pair members 18. The first binding pair member 16 and the one or more second binding pair members 18 may each be complementary members of a specific binding pair as are known in the art such as: antigen-antibody; enzyme-substrate; polynucleotide interactions, and the like. Exemplary binding pair members 16, 18 are set forth in U.S. Pat. No. 7,842,475, the entirety of which is hereby incorporated by reference herein.

The sample 20 may be any suitable material suspected of having the target analyte, e.g., second binding pair member 18. In an embodiment, the target analyte may be any molecule found directly in a sample such as biological tissue, including body fluids, from a suitable subject. The subject may be any human or non-human mammal such and the biological sample may comprise whole blood, serum, plasma, sputum, lymphatic fluid, semen, vaginal mucus, feces, urine, spinal fluid, saliva, stool, cerebral spinal fluid, tears, mucus, and the like; biological tissue such as hair, skin, sections or excised tissues from organs or other body parts; and so forth. The sample 20 may undergo any pretreatment or preparation necessary to submit the sample to the solid support 10 as would be appreciated by one skilled in the art.

Aspects of the present invention herein are directed to processes to determine that sufficient binding sites exist for attachment of the first binding pair member 16. Thus, referring again to FIG. 1, it may be critical to know the number of surface functional groups 12 on the solid support 10 and/or the number of functional groups associated with the linking agent 14 available for bonding to the first binding pair member 16. During preparation of the solid support 10 for immobilizing first binding pair member 16 thereon, it may be useful to know the number of surface functional groups and/or linking agents that are immobilized on the solid support 10. Further, prior to introduction of the first binding pair member 16 for immobilization on the support, knowledge of the number of binding sites available beforehand may assist with providing an effective amount of the first binding pair member 16. To reiterate, too few first binding pair members 16 for the number of functional groups available for binding thereto may result in an unsaturated solid support 10 incapable of detecting the target analyte, especially at higher concentrations in the detectable range. Meanwhile, the processes described herein may prevent the addition of an excessive amount of the binding pair member 16, thereby resulting in waste during manufacture of like solid supports.

Figure 2:
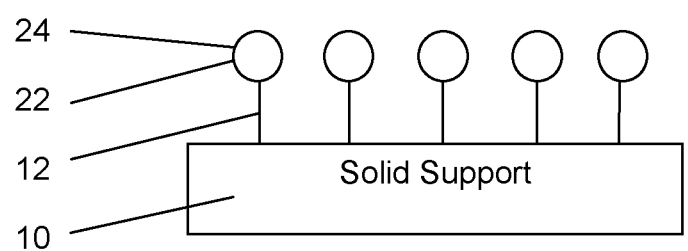
FIG. 2 illustrates a solid support having surface functional groups and a selective compound bound to the surface functional groups in accordance with an aspect of the present invention.
Figure 3:
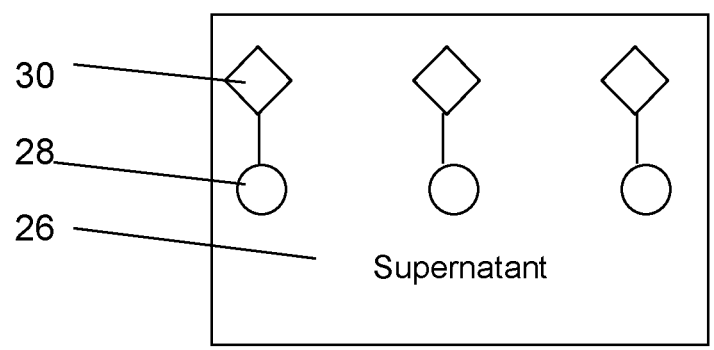
FIG. 3 illustrates a supernatant comprising a selective compound bound to an indicator in accordance with an aspect of the present invention.

Referring now to FIGS. 2-3, there are illustrated components utilized in a method for determining a number of functional groups on a solid support in accordance with an aspect of the present invention. In certain embodiments, one or more of the components may be provided as a kit and may further include packaging and/or instructions fixed in a tangible form for carrying out a method as described herein.

In the embodiment of FIG. 2, there is shown a solid support 10 having surface functional groups 12 as was described above. In addition, a selective compound 22 is provided which may bind to, by covalent bonding or otherwise, to the surface functional groups 12 (shown as immobilized selective compound 24). During this interaction between the selective compound 22 and the functional groups 12, an amount of the selective compound 22 may not bind to the surface functional groups 12. This amount will be "free" and being unbound to support 10 can be captured in a byproduct 26, such as a supernatant. As shown in FIG. 3, there is shown a byproduct 26 which comprises an amount of unbound selective compound 28. To this byproduct 26, an indicator 30 is provided which may bind to the unbound selective compound 28 to provide a measurable result. The process for determining an amount of the functional groups 12 utilizing the selective compound 22, 28 and indicator 30 will be described in detail further below.

Figure 4:
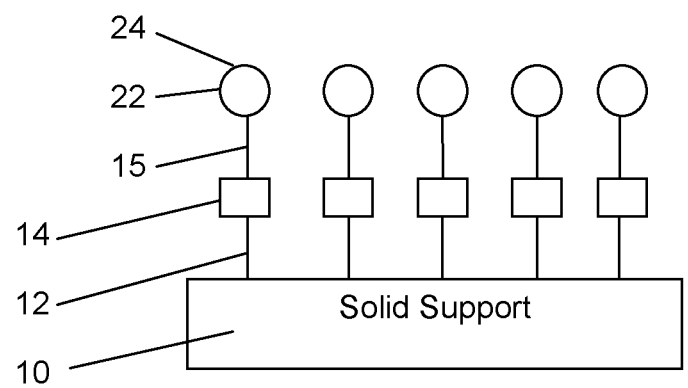
FIG. 4 illustrates a solid support having a linking agent and a selective compound bound to a linking agent in accordance with an aspect of the present invention.

In another embodiment, as shown in FIG. 4, there is shown a solid support 10 having a linking agent 14 bonded to the solid support 10 via surface functional groups 12. In this embodiment, the selective compound 22 is thus one which may bind to, by covalent bonding or otherwise, to functional groups 15 of the linking agent 14 to provide immobilized selective compound 24. Further, in this embodiment, during the contacting between the selective compound 22 and the functional groups 15, it is also appreciated that an amount of the selective compound 22 may not bind to the surface functional groups 12. This amount will be "free" and may be captured in a byproduct 26, such as in a supernatant. Referring again to FIG. 3, the byproduct 26 can be collected and thus comprises an amount of unbound selective compound 28. To this byproduct 26, an indicator 30 is provided which may bind to the unbound selective compound 28 in the byproduct 26 to provide a measurable result. The process for determining an amount of the functional groups 15 on the linking agents 14 utilizing the selective compound 22, 28 and indicator 30 will also be described in detail further below.

Figure 5:
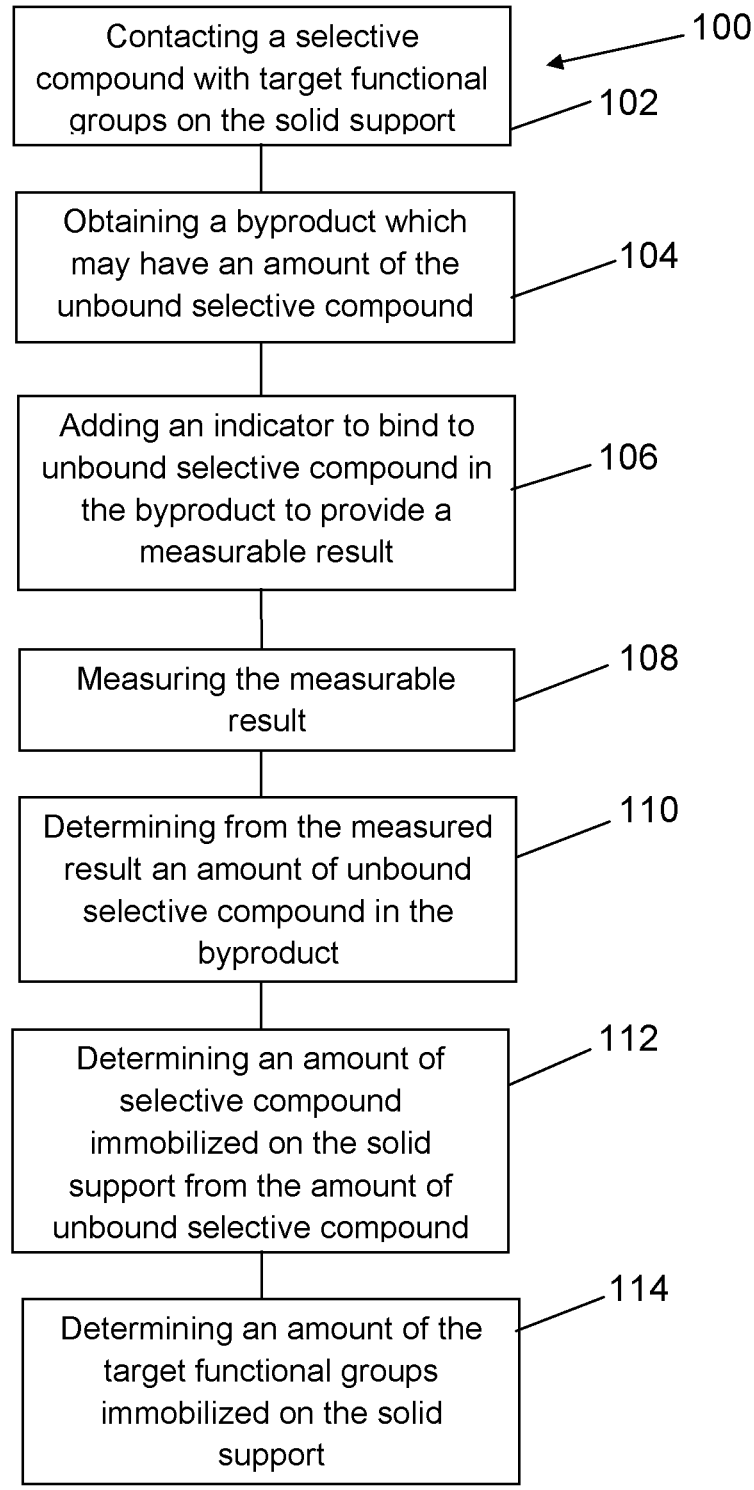
FIG. 5 illustrates a method for determining a number of functional groups on a solid support in accordance with an aspect of the present invention.

Referring now to FIG. 5, there is shown a method 100 for quantifying an amount of target functional groups on a solid support 10. It is understood that the term "target functional groups" may include any functional groups directly or indirectly immobilized the solid support 10, and thus may refer surface functional groups 12 or functional groups 15 on a linking agent 14 as described above. For purposes of the method 100, one set of target functional groups to quantify may be selected. In an embodiment, the target functional groups are surface functional groups 12 on the solid support 10, which have been immobilized on the solid support 10 by a reaction which adds the functional groups 12 directly to the solid support 10. For example, immobilized amino functional groups may be provided by a reaction between an aminosilane compound and the solid support 10. In other embodiments, the target functional groups are present on the linking agent 14 and bind to surface functional groups 12 on the solid support 10. In addition, the linking agent 14 comprises target functional groups for binding with the first binding pair member 16. The target functional groups may comprise amino functional groups, aldehydic functional groups, or any other functional groups described herein. The functional groups of the linking agent 14 for binding to both the solid support 10 and the first binding pair member 16 may be the same, but it is the understood that the present invention is not so limited.

In an embodiment, the method 100 comprises step 102 of contacting the target functional groups immobilized on the solid support 10 with an effective amount of a selective compound 22. This contacting results in at least some of the selective compound 22 being bound to the solid support 10 via the target functional groups (12 or 15) and a byproduct 26 (e.g., a supernatant) comprising unbound selective compound 22 (if any). The contacting step 102 may take place at a suitable temperature, e.g., room temperature to 50° C., and for a suitable time period, e.g., from 1 to 96 hours, for the binding to complete. Further, the contacting step 102 may take place in a suitable vessel. In an embodiment, the contacting comprises reacting the selective compound 22 and the target functional groups (12 or 15).

In an embodiment, the method 100 may thus further include step 104 of obtaining the byproduct 26, which may have an amount of the unbound selective compound 28. In an embodiment, the byproduct 26 may comprise a supernatant having an amount of the selective compound 22, which did not bind (covalently or otherwise) to the target functional groups ("unbound selective compound 28"). In a particular embodiment, the components may be added to a vessel, placed in an incubator, and mixed for a suitable amount of time. Thereafter, a resulting byproduct 25 such as a supernatant may be separated from the solid support 10 by magnetic separation, centrifugation, or the like.

To determine the amount of the unbound selective compound 28, the method 100 may further comprise step 106 of adding an indicator 30 to bind to the unbound selective compound 28 in the byproduct 26 (e.g., supernatant) to provide a measurable result. The addition of the indicator 30 may also take place at a suitable temperature, e.g., room temperature to 50° C., and for a suitable time period, e.g., from 1 to 96 hours, effective to provide the measurable result. Without limitation, the measurable result may comprise an absorbance value, a fluorescence value, and an electrical current signal value. In certain embodiments, the measurable result may comprise a colorimetric result.

Accordingly, the indicator 30 may be any suitable compound to bring about a measurable result. For example, the indicator 30 may comprise a member selected from the group consisting of propylamine, propionaldehyde, and 2, 4, 6-trinitrobenzene sulfonic acid (TNBSA) to provide a colorimetric result. Moreover, individual ones of these indicators may be more suitable than others for particular functional groups/selective compounds. For example, propionaldehyde may be a suitable indicator 30 when the unbound selective compound 28 comprises one with one or more amino groups thereon which will react with the aldehydic selective compound. In turn, it is appreciated that the selective compound 22 may be any compound which binds at least temporarily to a target functional group and to which the indicator 30 may bind. In this way, the indicator 30 may provide a measurable signal indicative of an amount of selective compound associated therewith.

Following addition of the indicator 30, the method 100 may further include step 108 of measuring the measurable result. The measurement may be taken using suitable instrumentation known in the art such as a microplate well reader which utilizes a selected detection mode. Common detection modes include but are not limited to absorbance, fluorescence intensity, luminescence, time-resolved fluorescence, and fluorescence polarization. The detectors may be part of a system that also comprises a computing unit comprising one or more modules configured to receive data from the detectors and determine at least one result from the data. The system may also add any or all of the components for the methods according to instructions provided by the computing unit. In this way, the computing unit may also function as an electronic control circuit. The computing unit may comprise, for example, a special purpose computer comprising a microprocessor, a microcomputer, an industrial controller, a programmable logic controller, a discrete logic circuit or other suitable controlling device. In an embodiment, the computing unit may further comprise one or more input channels, a memory, and output channel(s). The memory may include a computer-readable medium or a storage device, e.g., floppy disk, a compact disc read only memory (CD-ROM), or the like. In an embodiment, the computing unit may comprise computer readable instructions for performing any aspect of the methods or for controlling any aspect of the components described herein.

In an embodiment, the method 100 further comprises step 110 of determining from the measured result an amount of unbound selective compound 28 in the byproduct 26. The amount of the unbound selective compound 28 may be determined via the use of known standards and controls as would be well understood by persons skilled in the art. For example, results may be compared to values of a calibration curve created from a plurality of standard samples having predetermined concentrations as is known in the art.

Further, the method 100 may include step 112 of determining an amount of immobilized selective compound 24 immobilized on the solid support 10 from the amount of unbound selective compound 28 in the byproduct 26, e.g., supernatant. The amount of immobilized selective compound 24 may be determined via calculating a difference between a starting concentration of selective compound 22 added for the contacting step 102 and the determined amount of unbound selective compound 28 (from step 110). The amount of immobilized selective compound 24 on the solid support 10 will be that amount bound (e.g., covalently bonded or otherwise) to the surface functional groups 12 or functional groups 15 on the linking agents 14 depending on the particular design of the process.

Still further, the method may include step 114 of determining from the amount of the immobilized selective compound 24 an amount of the target functional groups immobilized on the solid support 10. Thus, from the amount of immobilized selective compound 24, the corresponding number of target functional groups (e.g., functional groups 12 or 15) may be determined. For example, in certain embodiments, one immobilized selective compound 24 may correspond to one target functional group on the solid support 10. Alternatively, one immobilized selective compound 24 may correspond to two or more functional groups on the solid support 10. In certain embodiments, the number of target functional groups may be expressed as the number of equivalents of the particular functional groups.

By way of example only, two specific embodiments will be explained in brief detail below, although it is understood that the present invention is not so limited.

In a first particular embodiment, the solid support 10 comprises surface functional groups 12, e.g., immobilized aldehydic functional groups. Thus, in this instance, one objective of the method may be to determine the number of aldehydic functional groups on the solid support 10. To accomplish this, the aldehydic functional groups may be immobilized on the solid support 10 by a reaction which adds the aldehydic functional groups to existing amino groups on the solid support 10. In this embodiment, the solid support 10 may comprise amino-functionalized paramagnetic particles, which are readily commercially available. In addition, in a particular embodiment, the aldehydic functional groups may be immobilized on the solid support 10 via a reaction between glutaraldehyde and the amino groups on the solid support 10.

In a next step, a selective compound 22 which selectively reacts with the immobilized aldehydic functional groups may be added to a vessel comprising the solid support 10, mixed, and incubated for an effective amount of time. In this instance, the selective compound 22 may be one which readily reacts with the immobilized aldehydic functional groups such as an amino-containing compound. In an embodiment, the selective compound 22 comprises propylamine. After reaction between propylamine and the immobilized aldehydic functional groups, propylamine should ideally react with substantially all to all of the available aldehydic functional groups provided sufficient propylamine was present. The reaction may take place under suitable conditions effective to react the components to completion and produce a supernatant. The remaining unbound propylamine may be disposed within a byproduct 26 such as a supernatant.

To this supernatant, an indicator 30 is added which, in this instance, will react with the unbound propylamine in the supernatant. In this embodiment, the inventors have found that 2,4,6-trinitrobenzene sulfonic acid (TNBSA) works as a suitable indicator. TNBSA is a commercially available reagent used to quantitate amino groups. The reaction of TNBSA with amines generates a highly chromogenic product that can be readily measured at a peak wavelength of 335 nm, or more conveniently at 405 nm when using a microplate. From the resulting measurements, the amount of bound and unbound propylamine in this instance may be determined as described above, and the number of aldehydic functional groups on the solid support 10 may be determined therefrom.

In a second particular embodiment, the solid support 10 comprises functional groups 12, e.g., immobilized amino functional groups. Thus, in this instance, one objective of the method is to determine the number of amino functional groups on the solid support 10. To accomplish this, as mentioned above, PMP may be reacted with an aminosilane produce amino-functionalized PMP.

In a next step, a selective compound which selectively reacts with the immobilized amino functional groups may be added to a vessel comprising the solid support 10, mixed, and incubated. In this instance, the selective compound 22 may be one which readily reacts with the immobilized amino functional groups such as an aldehyde compound. In an embodiment, the selective compound comprises propionaldehyde. After reaction between propionaldehyde and the immobilized amino functional groups, propionaldehyde should ideally react with available amino functional groups provided sufficient propionaldehyde was present. As in the above example, the reaction may take place under suitable conditions effective to produce a supernatant. In this instance, remaining unbound propionaldehyde may be disposed within the supernatant.

To this supernatant, an indicator 30 is added which, in this instance, will react with the unbound propylamine in the supernatant. In this embodiment, the inventors have found that a solution comprising PURPALD® (4-Amino-3-hydrazino-5-mercapto-1,2,4-triazole, 4-Amino-5-hydrazino-1,2,4-triazole-3-thiol), available from Sigma-Aldrich (St. Louis, Mo.), works as a suitable indicator. TNBSA is a commercially available reagent used to quantitate amino groups. The reaction of PURPALD® with carbonyl groups generates a highly chromogenic product. In an embodiment, the resulting product has a maximum absorption at 490-540 nm. From the resulting measurements, the amount of bound and unbound propionaldehyde may be determined as described above, and the number of immobilized amino functional groups on the solid support 10 may be determined therefrom.

In either case, following determination of the number of immobilized functional groups, an effective amount of the first binding pair member 16 may be reacted with the immobilized functional groups 24 on like solid supports 10. In an embodiment, based on the determined number of target functional groups on the solid support 10, additional target functional groups may be added to the solid support 10 if the determined number of target functional groups on the solid support 10 is less than a predetermined value. The predetermined value may be that number of target functional groups necessary to directly or indirectly bind a predetermined amount of the first binding pair members 16. In another embodiment, based on the determined number of target functional groups on the solid support 10, one or more additional solid supports may be manufactured which comprise a stoichiometric amount of the first binding pair member 16 bound to the target functional groups. As a result, the determined number of functional groups by the processes described herein may be utilized as a guide to determine optimum manufacturing of solid supports.

In another aspect, a kit may be provided comprising any components necessary for carrying out a method or process as described herein. In an embodiment, the kit comprises the selective compound which selectively binds to the target functional groups; and an indicator which selectively binds to the selective compound as described herein. In another aspect, the kit may comprise packaging and/or instructions for carrying out a method as described herein. The instructions may be printed or otherwise fixed, recorded, and/or saved on a tangible medium.

Aspects of the present invention are demonstrated by the following examples, which are not intended to be limiting in any manner.

EXAMPLE 1

Determination of the Incubation Time Required for Quantitation of Amino Equivalences of Paramagnetic (PMP) Particles Sample Preparation:

Two lots of Siemens' amine-functionalized paramagnetic particles (AHI-PMP) were used for the time-dependence studies. To 800 mg of each lot, 5×40 mL 25 mM sodium borate (pH 10.0, prepared from sodium borate, decahydrate, Sigma Cat. #S9640) was used to wash the particles in a 50-mL Falcon Tube. Supernatant was removed after a magnetic separation using DynaMag-50 (Life Technologies/Thermo Fisher) or an equivalent, and resuspended with 40 mL buffer after the last wash. 5 mL were equally aliquoted into each of eight 15-mL Falcon tubes @100 mg each.

To each tube was added 1.6 mL of 50 mM propionaldehyde (Sigma) in water. The tubes were filled to 8 mL with 25 mM borate (pH 10.0). Tubes which had 100 mg PMP with 10 mM propionaldehyde were placed in a 50° C. incubator and mixed on an orbital mixer. At the following time points: 1, 2, 3, 5, 15, 24, 48 and 72 hours, one tube each was removed and magnetic separation was performed using DynaMag-15 or an equivalent. The supernatant was saved from each tube.

Zero to 2.5 mM propionaldehyde standard samples in water were prepared and ¼ dilutions of supernatant samples in water were prepared. Each sample was pipeted into a 0.5 mL microfuge tube and an appropriate tube holder was used so that an 8- or 12-multi-chanel pipet could aspirate. When these preparations were completed, 7 mg/mL of PUR-PALD® (Sigma-Aldrich, St. Louis, Mo.) was dissolved in 1 M NaOH and vortexed. Thereafter, 1% volume of 0.3% hydrogen peroxide (ACROS Organics) was mixed in. With a multi-channel pipet, 200 µL of the PURPALD®/NaOH/hydrogen peroxide solution was transferred into each of a plurality of wells, followed by 50 µL of standard samples and supernatant samples. The samples were mixed on an orbital rotator mixer for 10 to 30 minutes at room temperature. When the standard colors appeared to be increasing strength by way of an increasing pink color, the microplate was moved to a microplate reader (e.g., Molecular Devices' Vmax kinetic microplate reader) and read at 490 nm.

Figure 6:
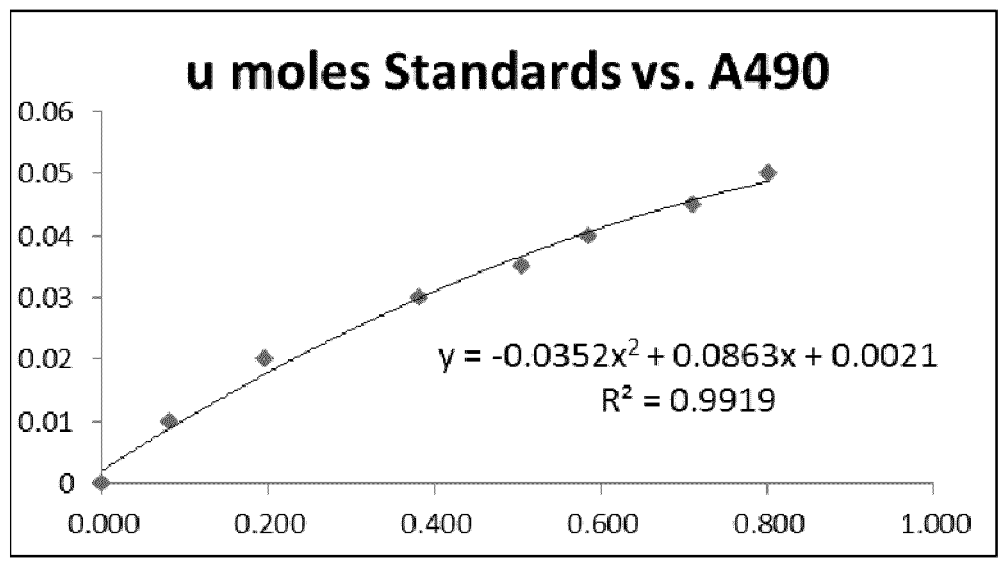
FIG. 6 is a graph showing concentrations of propionaldehyde standards vs. absorbance in accordance with an aspect of the present invention.

Results:

As shown in FIG. 6, the average absorbance at 490 nm for 8 separate standards (assayed in triplicate) were plotted and a quadratic fitting equation of µ mole aldehyde vs. absorbance was established. The quadratic fitting equation was used to calculate the unbound µ moles of propionaldehyde, which was then used to calculate the µ moles of aldehyde bound. The µ moles of aldehyde bound to the PMP were equivalent to the amino equivalence of amines on PMP, after a correction from dilution factors.

Figure 7:
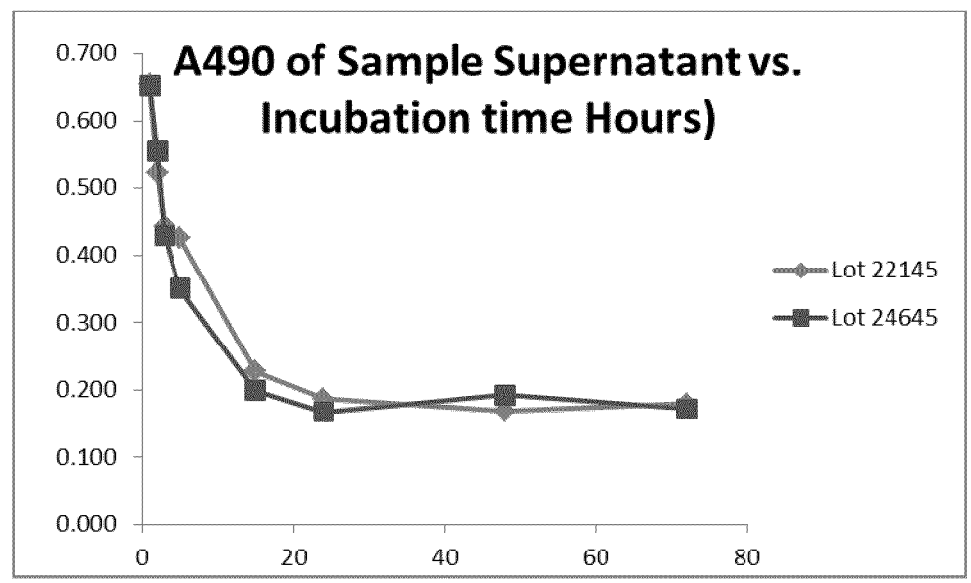
FIG. 7 is a graph showing absorbance of sample supernatants from time dependence studies in accordance with another aspect of the present invention.

In addition, as shown in FIG. 7, after 24 hours of PMP reaction with propionaldehyde, Schiff base formation was completed indicating that the determination of the amino equivalences may be carried out at 50° C. incubator on a mixer for at least 24 hours.

EXAMPLE 2

Determination of the Amino Group Equivalences of 12 Lots PMP

Sample Preparation

Twelve lots of PMP from Siemens Healthcare Diagnostics Inc. were obtained. 100 mg of material from each lot was placed in a separate 15-mL Falcon Tube and washed with 5×10 mL 25 mM sodium borate (pH 10.0). Supernatant was removed after magnetic separation using DyneMag-15 or an equivalent and then re-suspended with 5 mL buffer after the last wash.

To each tube was added 1.6 mL of 50 mM propionaldehyde (Sigma) in water. The tubes were filled to 8 mL with 25 mM borate (pH 10.0). The tubes which had 100 mg PMP with 10 mM propionaldehyde were placed in a 50° C. incubator and mixed on an orbital mixer for 72 hours. All tubes were removed and magnetic separation was performed using DyneMag-15 or an equivalent. The supernatant was saved from each tube.

Assay on a 96-Well Microplate

Zero to 2.5 mM propionaldehyde standard samples were prepared in water and ¼ dilutions of supernatant samples were prepared in water. Each sample (standards and supernatants) was pipeted into a 0.5 mL microfuge tube and an appropriate tube holder was used so that an 8- or 12-multichanel pipet could aspirate. Thereafter, 7 mg/mL of PUR-PALD® (catalog number 162892-25G, Sigma-Aldrich, St. Louis, Mo.) was dissolved in 1 M NaOH and vortexed to dissolve completely. 1% volume of 0.3% hydrogen peroxide (ACROS Organics catalog number 426001000) was mixed into the PURPALD® solution. With the multichannel pipet, 200 µL of the PURPALD®/NaOH/hydrogen peroxide was transferred into wells, followed by 50 µL of standards and samples. Thereafter, the samples/standards were mixed on an orbital rotator mixer for 10 to 30 min at room temperature. When an increasing pink color appeared, the microplate was moved to a microplate reader (e.g., Molecular Devices' Vmax kinetic microplate reader) and read at 490 nm.

Results

Figure 8:
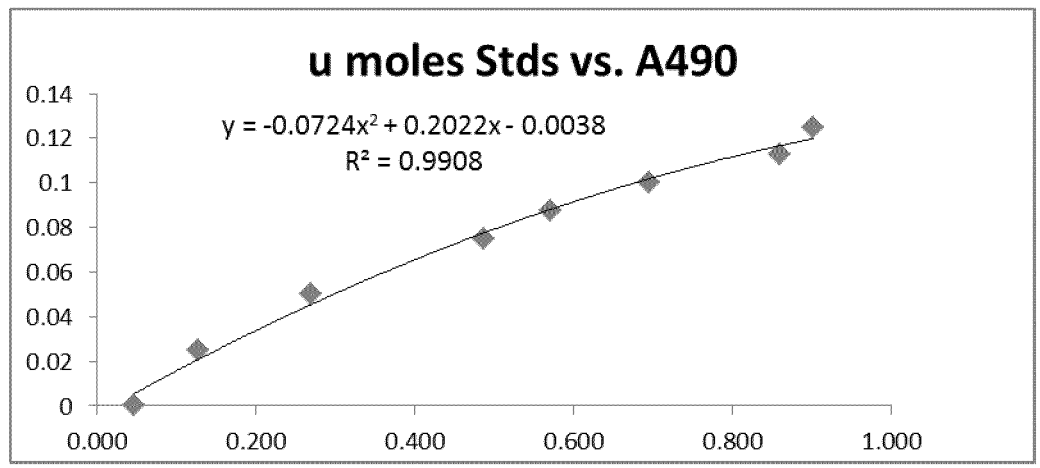
FIG. 8 is a graph showing concentrations of propionaldehyde standards vs. absorbance in accordance with another aspect of the present invention.

As shown in FIG. 8, the average absorbance of 8 standards (assayed in triplicates) were plotted and a quadratic fitting equation of p mole aldehyde vs. absorbance at 490 nm was established. The fitting equation was used to calculate the unbound μ moles of propionaldehyde, which, in turn, was used to calculate the μ moles of propionaldehyde bound. The μ moles of propionaldehyde bound was equivalent to the amino equivalence on the PMPs. The μ moles of amino equivalences per mg of PMP were thus determined. It was shown that the tested lots had about the same amino equivalences per mg of solid.

EXAMPLE 3

Determination of the Incubation Time Required for Quantitation of Aldehyde Equivalences of PMP-CHO Particles Sample Preparation:

Eight hundred mg of amino-functionalized PMP (Siemens Healthcare Diagnostics Inc.) were buffer exchanged with 0.1 M sodium phosphate (pH 7.5) and activated by 6.25% glutaraldehyde (Polysciences Catalog #1909) at 50 mg solid/mL for 3 hours and mixed by a Glas-Col 3D orbital shaker (3D) for 3 hours to PMP-CHO particles. The unbound glutaraldehyde was washed off by 4×56 mL with 0.1 M sodium phosphate (pH 7.5). The PMP-CHO's were re-suspended in the new polypropylene bottles at 20 mg solid/mL in the same buffer.

One hundred mg of the PMP-CHO were aspirated to each of eight 15 mL-Falcon tubes, were washed by 5×10 mL of 25 mM sodium borate (pH 10, prepared from sodium borate, decahydrate, Sigma Catalog #S9640), and then re-suspended in 5 mL of the same buffer. To each tube was added 1.6 mL of 50 mM propylamine (Sigma cat #240958) in water and filled to 8 mL with 25 mM sodium borate (pH 10), which resulted in the mixing of the solid with 10 mM propylamine. The 8 tubes are incubated for 0-72 hours in a 50° C. incubator. At each time point, the supernatant was separated by a DynaMag-15 or an equivalent magnet and mixed with an equal volume of 78 mM HEPES (Sigma catalog #H3375, pH not adjusted) to reach a final pH of ~8.5+/−0.2. The centrifuged supernatants were kept at 2-8° C. until all time points were completed.

Assay on a 96-Well Microplate:

Ten mL of mixed buffer was prepared by mixing 5 mL of 25 mM sodium borate (pH 10), and equal volume of 0.5 M sodium bicarbonate (pH 7.9) to reach a pH of ~8.8. 5 mM of propylamine standards were prepared by mixing equal volumes of 10 mM of propylamine and 78 mM HEPES, then diluting to 0-5 mM propylamine in the mixed buffer. 200 μL of standards were aspirated in triplicate into 96 microplate wells. In addition, 200 μL of samples were aspirated in hexaplicate into 96 microplate wells. To each of standard and 3 of the sample wells was added 50 μL of 0.01% TNBSA (or Picrylsulfonic solution, Sigma cat #92823). 50 mM sodium borate (pH 8.5). 50 μL of 50 mM sodium borate (pH 8.5) was added only to sample controls. The samples were mixed on a shaker at room temperature for ~60 min. When the well solutions turned yellow to orange color to appropriate intensities (absorbance ~0.5 to 1), the plate with wells was moved to a microplate reader such as Molecular Devices' Vmax kinetic microplate reader, and read at 405 nm.

Results:

Table 2 below shows the A405 and μ moles aldehyde measured at each time point.

TABLE 2

Summary of the A405 and μ moles aldehyde/g PMP-CHO measured at time points

| Incub time hrs | A405 | BKG | Net A405 | u moles unbound | u moles bound | Dil factor | mg PMP | umole/mg |
|---|---|---|---|---|---|---|---|---|
| 0 | 0.7095 | 0.0456 | 0.7083 | 1 | 0 | 80 | 100 | 0 |
| 1.5 | 0.6890 | 0.047 | 0.6423 | 0.8536 | 0.1464 | 80 | 100 | 0.117 |
| 3 | 0.6710 | 0.054 | 0.6173 | 0.8085 | 0.1915 | 80 | 100 | 0.153 |
| 16 | 0.6670 | 0.071 | 0.5963 | 0.7713 | 0.2287 | 80 | 100 | 0.183 |
| 24 | 0.6630 | 0.076 | 0.5870 | 0.7550 | 0.2450 | 80 | 100 | 0.196 |
| 42 | 0.6610 | 0.077 | 0.5843 | 0.7504 | 0.2496 | 80 | 100 | 0.200 |
| 48 | 0.6570 | 0.076 | 0.5810 | 0.7446 | 0.2554 | 80 | 100 | 0.204 |
| 72 | 0.6610 | 0.077 | 0.5843 | 0.7504 | 0.2496 | 80 | 100 | 0.200 |

Figure 9:
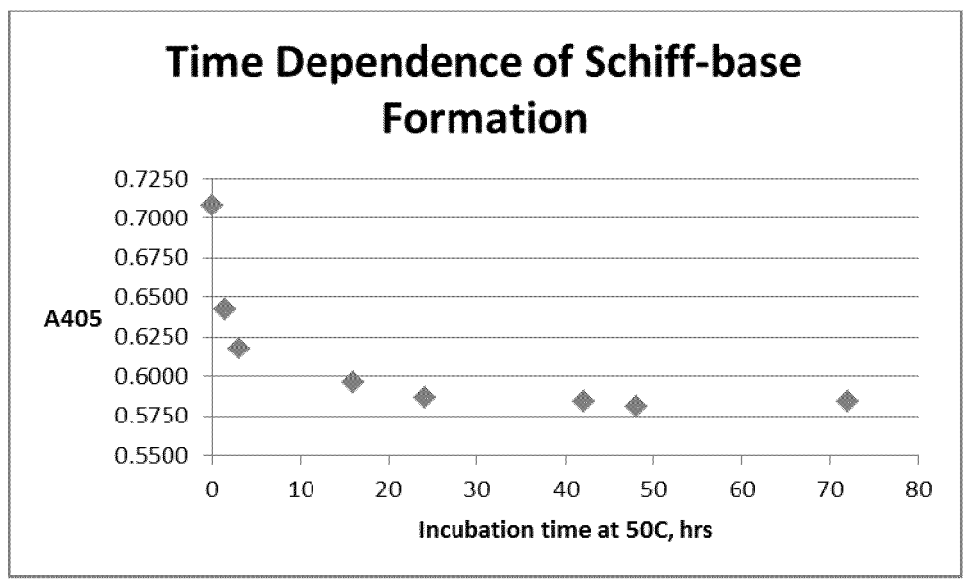
FIG. 9 is a graph showing time dependence of Schiff-base formation for aldehyde quantitation in accordance with an aspect of the present invention.

FIG. 9 further shows the dependence of Schiff-base formation for aldehyde quantitation. In particular, the results indicated that at 22+/2 hours incubation at 50° C., the reaction reaches completion.

EXAMPLE 4

Determination of the Aldehyde Group Equivalences of PMP-CHO Using Propylamine and Trinitrobenzene Sulfonic Acid (TNBSA)

Sample Preparation:

Two grams of PMP (Siemens Healthcare Diagnostics Inc.) were buffer exchanged with 0.1 M sodium phosphate (pH 7.5) and activated by 6.25% glutaraldehyde (Polysciences Cat #1909) at 50 mg solid/mL for 3 hours and mixed by a Glas-Col 3D orbital shaker (3D) or a Eberbach mixer (EB) at room temperature for 3 hours. The unbound glutaraldehyde was washed off by 4×140 mL with 0.1 M sodium phosphate (pH 7.5). The PMP-CHO's were re-suspended in the new polypropylene bottles at 20 mg solid/mL in the same buffer.

One hundred mgs in two 15 mL-Falcon tubes, labeled as 3D and EB, were washed by 5×10 mL of 25 mM sodium borate (pH 10, prepared from sodium borate, decahydrate, Sigma Cat#S9640) then re-suspended in 5 mL of the same buffer. To each tube was added 1.6 mL of 50 mM propylamine (Sigma cat#240958) in water and the tubes were filled to 8 mL with 25 mM sodium borate (pH 10), which resulted in the mixing of the solid with 10 mM propylamine. The two tubes were incubated for 24 hours in a 50° C. incubator. The supernatants were then separated by a DyneMag-15 or an equivalent magnet then mixed equal volume of 78 mM HEPES (Sigma catalog #H3375, pH not adjusted) to reach a final pH of ~8.5+/−0.2. 10 mM propylamine stock was prepared the same way as the samples except no PMP-CHO is present.

Assay on a 96-Well Microplate:

Ten mL of mixed buffer was prepared by mixing 5 mL of with equal volume of 25 mM sodium borate (pH 10), and equal volume of 0.5 M sodium bicarbonate (pH 7.9) to reach a pH of ~8.8. 5 mM propylamine standard samples were prepared by mixing equal volumes of propylamine and 78 mM HEPES first then diluted to 0-5 mM propylamine in the mixed buffer. 200 μL of standard samples were aspirated in triplicate into 96 Microplate wells. 200 μL samples were aspirated in hexaplicate into 96 Microplate wells. To each standard sample and 3 sample wells were added 50 μL of 0.01% TNBSA (or Picrylsulfonic solution, Sigma catalog #92823) in 50 mM sodium borate (pH 8.5) and 50 μL each of 50 mM sodium borate (pH 8.5) only to sample controls. The plate was mixed on a shaker at room temperature for ~60 min. When the well solutions turned from yellow to orange color and reached to appropriate intensities (absorbance ~0.5 to 1), the plate was moved to a microplate reader, such as Molecular Devices' Vmax kinetic microplate reader, and read at 405 nm.

Figure 10:
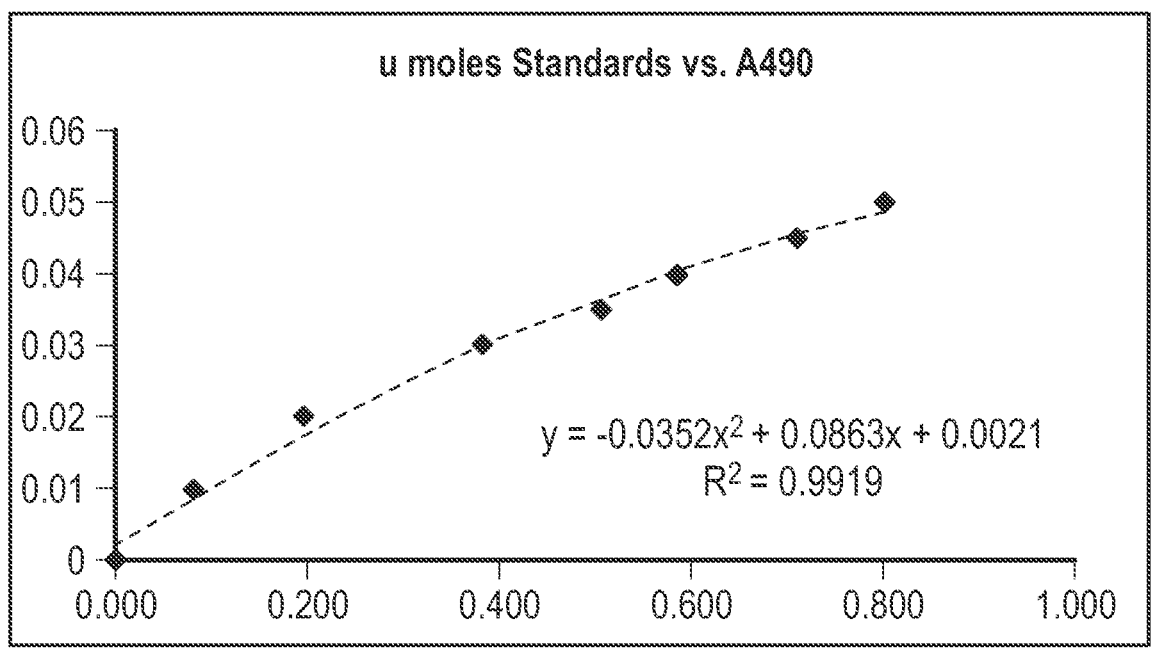
FIG. 10 is a graph showing concentrations of propylamine standards vs. absorbance in accordance with an aspect of the present invention.

Results:

FIG. 10 shows μ moles of propylamine standards vs. A405. Table 3 below shows the μ mole of aldehyde equivalences after subtracting the sample controls.

TABLE 3

Aldehyde equivalences of PMP-CHOs

| Sample # | ABS | umoles/mg PMP |
|---|---|---|
| 3D CHO-PMP | 0.485 | 0.1769 |
| EB CHO-PMP | 0.472 | 0.1951 |

EXAMPLE 5

DOE Design and Determination of the Aldehyde Group Equivalences of PMP-CHO Using Propylamine and TNBSA DOE Design:

DOE, Design of Experiments, version 17, a statistical method for design and analysis of experimental data is marketed by Minitab Inc. in State College, PA. A 3-factor full factorial design variable with a center point and a response variable are listed in below:

TABLE 4

DOE Design and Response Variables

| Design Variables | Low | High | Center |
|---|---|---|---|
| PMP, mg/mL | 7 | 70 | 38.5 |
| Glutaraldehyde, % | 1 | 12.5 | 6.75 |
| Vessel Occupancy, % | 10 | 90 | 50 |
| Response Variable | μ molar aldehyde equivalents/mg PMP | | |

Sample Preparation:

PMP ranged from 5 to 5.5 grams for 9 preparation conditions ($2^3+1=9$) in 1 L Nalgene square bottles. The PMP were washed and magnetically separated 3 times with wash buffer (10 mM sodium phosphate, pH 7.4). Supernatants were drained by pipet aspiration. To each wetcake, PMP containing residual buffer in various sizes of square Nalgene containers (0.25 to 8 L), is added to a calculated volume of diluted glutaraldehye and mixed at room temperature for 3 hours via 3-D orbital shakers manufactured by Glas-Col in Terre Haute, Ind.

After washing the PMP 2×, the PMP-CHO were transferred to new 1 L Nalgene square containers and washed another 4 times with wash buffer. The final PMP-CHO wetcake is re-suspended in the 0.5 L Nalgene square bottles with the wash buffer to reach 20 mg/mL and stored at 2-8° C. until assayed.

Assay on a 96-Well Microplate:

Prior to conducting assay on a microplate, 100 mg each of the samples were incubated with 10 mM propylamine in 25 mM sodium borate (pH 10) for 24 hours at 50° C. using the assay protocol set forth in Example 5 above.

Results:

Table 5 summarizes the sample conditions and the response variable values and

TABLE 5

A summary on DOE Design and Response Variable Values

| StdOrder | RunOrder | CenterPt | Blocks | PMP mg/mL | GA % | Vessel Occupancy | umole CHO/mg |
|---|---|---|---|---|---|---|---|
| 8 | 1 | 1 | 1 | 70 | 12.5 | 79 | 0.1165 |
| 6 | 2 | 1 | 1 | 70 | 1 | 79 | 0.0731 |
| 9 | 3 | 0 | 1 | 38.5 | 6.75 | 41.5 | 0.1059 |
| 4 | 4 | 1 | 1 | 70 | 12.5 | 4 | 0.138 |
| 1 | 5 | 1 | 1 | 7 | 1 | 4 | 0.0872 |
| 2 | 6 | 1 | 1 | 70 | 1 | 4 | 0.0785 |
| 3 | 7 | 1 | 1 | 7 | 12.5 | 4 | 0.1158 |
| 7 | 8 | 1 | 1 | 7 | 12.5 | 79 | 0.125 |
| 5 | 9 | 1 | 1 | 7 | 1 | 79 | 0.0879 |

Table 6 shows the fitting models from a statistical analysis. In particular, Table 6 shows the parameter values after fitting model reduction with % Glutaraldehyde (p=0.011<0.05) the only factor that is significant

TABLE 6

Analysis of Variance

| Source | DF | Adj. SS | Adj. MS | F-Value | P-Value |
|---|---|---|---|---|---|
| Model | 6 | .003952 | .000659 | 15.90 | .060 |
| Linear | 3 | .003601 | .001200 | 28.97 | .034 |
| PMP mg/mL | 1 | .000012 | .000012 | 0.29 | .644 |
| GA % | 1 | .003553 | .003553 | 85.76 | .011 |
| Ves Occu | 1 | .000036 | .000036 | 0.87 | .449 |
| 2-way Interactions | 2 | .000342 | .000171 | 4.13 | .195 |
| PMP mg/mL*GA % | 1 | .000173 | .000173 | 4.17 | .178 |
| PMP mg/mL*Ves Occu | 1 | .000169 | .000169 | 4.09 | .181 |
| Curvature | 1 | .000009 | .000009 | 0.21 | .690 |
| Error | 2 | .000083 | .000041 | | |
| Total | 8 | .004035 | | | |

Model Summary

| S | R-sq (adj) | R-sq (Pred) |
|---|---|---|
| .0064368 | 97.95% | 91.79% |

Figure 11:
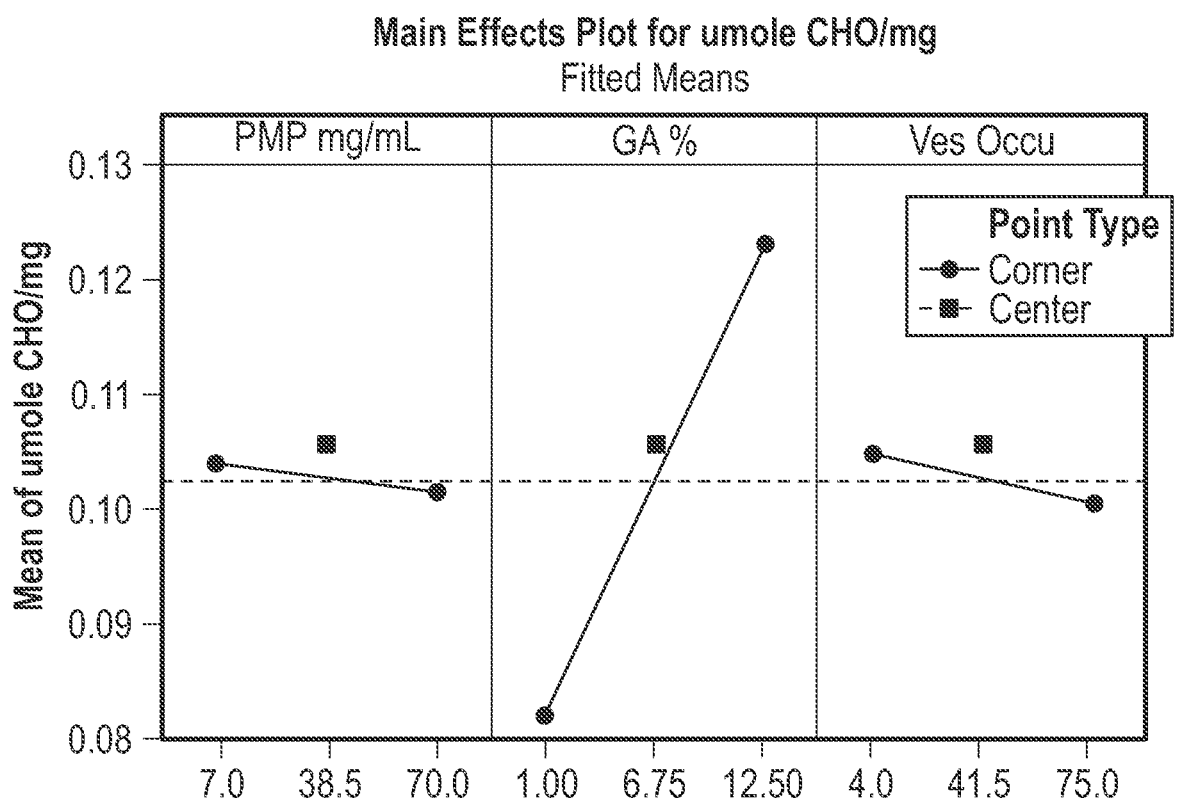
FIG. 11 is an effect plot indicating % glutaraldehyde as a main factor of aldehyde group formation in accordance with an aspect of the present invention.
Figure 12:
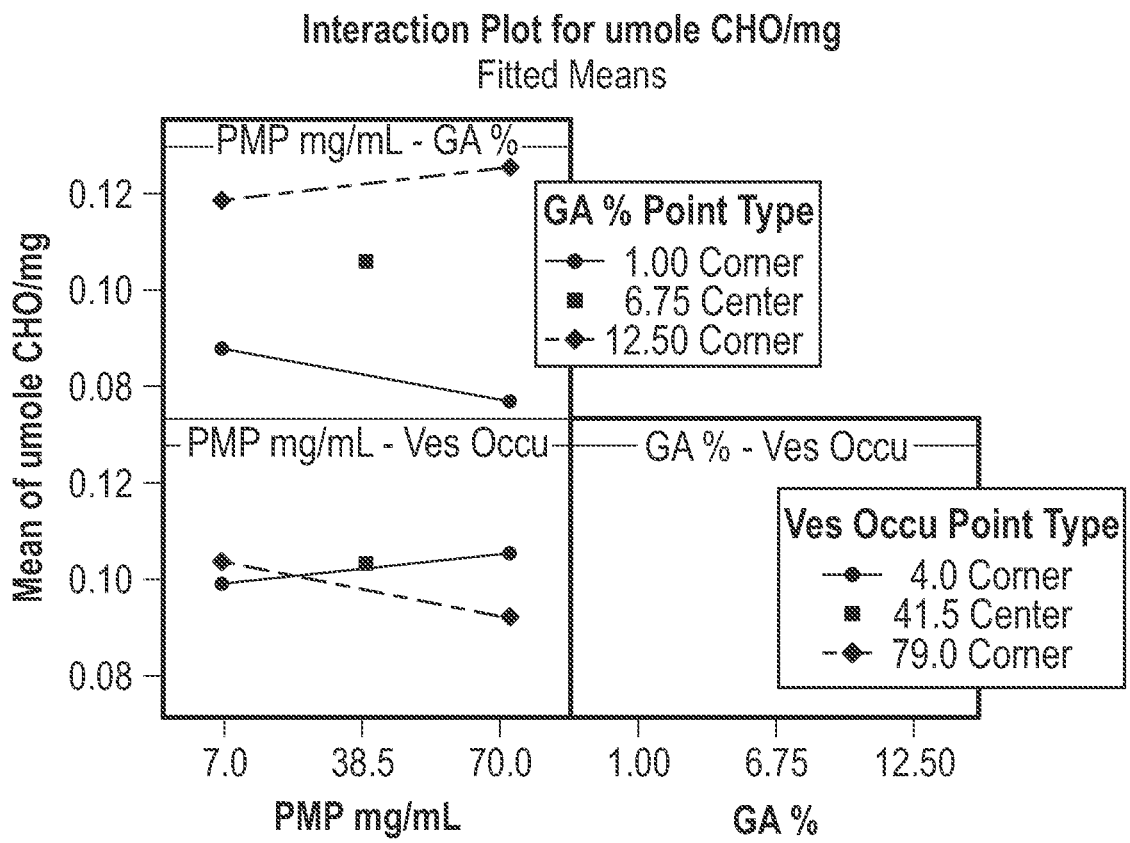
FIG. 12 is an interaction plot showing PMP mg/mL intersecting with % vessel occupancy in accordance with another aspect of the present invention.
Figure 13:
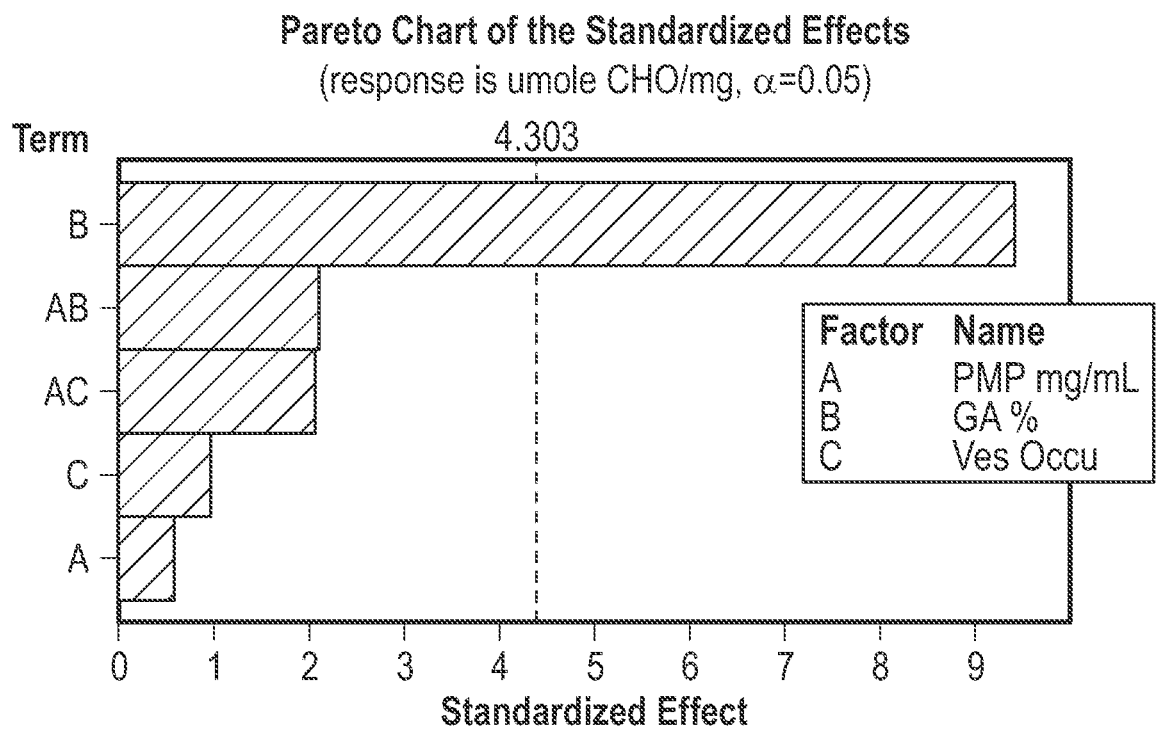
FIG. 13 is a Pareto Chart illustrating B (% glutaraldehyde) as a main effect of aldehyde group formation in accordance with another aspect of the present invention.

The results are further shown in accompanying FIGS. 11-13.

FIG. 11 is an effect plot indicating % glutarahyde is a main factor of aldehyde group formation.

FIG. 12 is an interaction plot showing PMP mg/mL intersecting with % Vessel Occupancy.

FIG. 13 is a Pareto Chart illustrating B (% Glutaraldehyde) is a main effect of aldehyde group formation.

Figure 14:
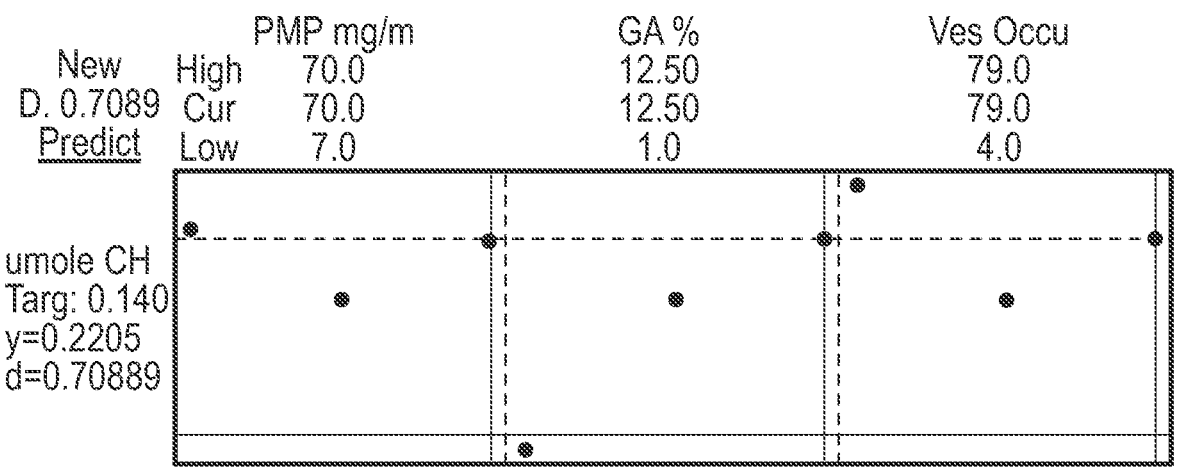
FIG. 14 illustrates optimal PMP concentration, glutaraldehyde concentration, and vessel occupancy to optimize aldehyde loading on PMP in accordance with another aspect of the present invention.

FIG. 14 illustrates that the Response Optimizer indicated that a D (Desirability) of 0.744 could be achieved with design variables set at 70 mg/mL. 12.5% Glutaraldehyde, and 79% Vessel Occupancy.

In conclusion, the experiment of Example 5 indicated indicates that by combining the Schiff-base formation between PMP-CHO and propylamine and a microplate test method with TNBSA, the optimization using DOE can be accomplished.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

The invention claimed is:

1. A method for quantifying target functional groups immobilized on a solid support comprising one or more paramagnetic particles, the method comprising the steps of:
    (a) contacting the target functional groups immobilized on the one or more paramagnetic particles with an amount of a selective compound, wherein an amount of the selective compound binds directly to the target functional groups and forms bound selective compound, and an amount of the selective compound does not bind to the target functional groups and is present as unbound selective compound, wherein the target functional groups comprise amino functional groups, and wherein the selective compound comprises an aldehydic compound which selectively reacts with immobilized amino functional groups on the one or more paramagnetic particles;
    (b) obtaining a byproduct having an amount of the unbound selective compound;
    (c) adding an indicator to the byproduct which binds to unbound selective compound in the byproduct to provide a colorimetric result, wherein the indicator comprises 4-Amino-3-hydrazino-5-mercapto-1,2,4-triazole;
    (d) measuring the colorimetric result;
    (e) determining from the measured result an amount of unbound selective compound in the byproduct;
    (f) determining an amount of bound selective compound immobilized on the one or more paramagnetic particles from the amount of unbound selective compound; and
    (g) determining from the amount of the immobilized selective compound an amount of the target functional groups immobilized on the one or more paramagnetic particles; and
    (h) reacting the paramagnetic particles with an effective amount of a first member of a binding pair to attach the first binding pair member to the paramagnetic particles, wherein the effective amount of the first binding pair member is determined based upon the amount of target functional groups immobilized on the paramagnetic particles determined in step (g), and wherein a second member of the binding pair is a target analyte in a sample.

2. The method of claim 1, wherein the target functional groups are provided on a linking agent bonded to the one or more paramagnetic particles.

3. The method of claim 1, wherein the immobilized amino functional groups are provided by a reaction between an aminosilane compound and the one or more paramagnetic particles.

4. The method of claim 1, wherein the selective compound comprises propionaldehyde.

5. The method of any of claims 1, 2, 3, and 4, further comprising, prior to step (h):
    manufacturing an additional one or more paramagnetic particles comprising additional target functional groups immobilized on the one or more paramagnetic particles if the determined number of target functional groups on the one or more paramagnetic particles is less than a predetermined value.

6. The method of any of claims 1, 2, 3, and 4, wherein the effective amount of the first binding part member is a stoichiometric amount.

7. The method of claim 6, wherein the first binding pair member is an antigen, antibody, enzyme, substrate, or polynucleotide.

8. The method of any of claims 1, 2, 3, and 4, wherein the contacting the target functional groups with an amount of the selective compound comprises reacting the target functional groups with an amount of a selective compound.

* * * * *